United States Patent [19]

Schepky et al.

[11] Patent Number: 4,650,664
[45] Date of Patent: * Mar. 17, 1987

[54] ORAL MOPIDAMOL PREPARATION

[75] Inventors: Gottfried Schepky, Biberach; Rolf Brickl, Warthausen; Peter Gruber, Biberach; Jochen Schmid, Warthausen; Ursula Springmeier, Mietingen, all of Fed. Rep. of Germany

[73] Assignee: Dr. Karl Thomae GmbH, Biberach an der Riss, Fed. Rep. of Germany

[*] Notice: The portion of the term of this patent subsequent to Jan. 24, 2001 has been disclaimed.

[21] Appl. No.: 772,166

[22] Filed: Sep. 3, 1985

Related U.S. Application Data

[62] Division of Ser. No. 539,998, Oct. 7, 1983, Pat. No. 4,596,705.

[30] Foreign Application Priority Data

Oct. 9, 1982 [DE] Fed. Rep. of Germany ....... 3237575

[51] Int. Cl.$^4$ .......................... A61K 9/52; A61K 9/54
[52] U.S. Cl. .................................... 424/456; 514/962; 424/494
[58] Field of Search ..................................... 424/19–22, 424/37; 514/962

[56] References Cited

U.S. PATENT DOCUMENTS

| 4,361,546 | 11/1982 | Stricker et al. | 424/19 |
| 4,367,217 | 1/1983 | Gruber et al. | 424/19 |
| 4,427,648 | 1/1984 | Brickl et al. | 424/19 |

FOREIGN PATENT DOCUMENTS 0019586 11/1980 European Pat. Off. .

OTHER PUBLICATIONS

White, CA.95 #209646w (1981) of EPO 19586, Nov. 26, 1980.
Philp CA.81 #21051e (1974).
Paoloni CA.78 #245u (1973).
Gastpar CA.78 #69905b (1973).
Horch CA.75 #61747a (1971).
Gastpar CA.75 #61771x (1971).
Didisheim CA.75 #61768b (1971).

*Primary Examiner*—Shep K. Rose
*Attorney, Agent, or Firm*—Hammond, Littell, Weissenberger & Dippert

[57] ABSTRACT

This invention relates to vehicles for the administration of mopidamol. More specifically, this invention relates to a method of treating cardiovascular disorders, malignancy, or thrombosis in a host in need of such treatment which comprises administering to said host a cardiovascularly, antimetastic, or antithrombotic effective amount of a composition comprised of (i) mopidamol or an acid addition salt thereof and (ii) at least one pharmacologically acceptable acid or acid substance, the total amount of acid from acid addition salt present and acid or acid substance being in a ratio of at least about 1 acid equivalent to 1 mol of mopidamol or its acid addition salt.

20 Claims, 3 Drawing Figures

FIG. 2

ORAL MOPIDAMOL PREPARATION

This application is divisional of co-pending U.S. patent application Ser. No. 539,998, filed Oct. 7, 1983 now U.S. Pat. No. 4,596,705.

FIELD OF THE INVENTION

This invention relates to vehicles for the administration of mopidamol. More specifically, this invention relates to a mopidamol-containing pharmaceutical form with improved bioavailability and to the use of said pharmaceutical form in treating cardiovascular disorders, malignancy, and thrombosis.

BACKGROUND OF THE INVENTION

The compound 2,6-bis-(diethanolamino)-4-piperidinopyrimido[5,4-d]pyrimidine, known as mopidamol, is disclosed in U.S. Pat. No. 3,031,450, incorporated herein by reference. This compound has been successfully used as an active substance, such as an antimetastic agent, for many years. The pharmaceutical preparations previously known which contain this active substance have a number of disadvantages for certain applications due to the special physical properties of mopidamol.

Mopidamol is readily water-soluble only in an acidic medium, and therefore it can only go into solution from solid pharmaceutical forms and then be absorbed if the pharmaceutical preparations remain in the acidic range for a sufficiently long period. Thus, the solubility and hence also the absorption greatly depend upon the retention time and the pH in the stomach and upper intestinal tract. This results in sharp inter-individual and intra-individual fluctuations in the blood levels since the motility of a patient, the pH of the patient's stomach and intestines, and the patient's food intake have a considerably influence on absorption. In some patients the blood levels may even be so low that they practically amount to an absence of absorption.

The problems concerning administration of mopidamol are similar to those of a related compound, dipyridamole. Improved delivery pharmaceutical forms for dipyridamole are described in co-pending, U.S. patent application Ser. No. 389,282, filed June 17, 1982, now U.S. Pat. No. 4,427,638, incorporated herein by reference.

OBJECTS OF THE INVENTION

It is an object of the invention to provide vehicles for administering mopidamol.

It is also an object of the invention to provide mopidamol-containing pharmaceutical forms with improved bioavailability and a method for their use.

It is a further object of the invention to provide a method of treating cardiovascular disorders, malignancy, or thrombosis in a host in need of such treatment which comprises administering to said host an effective amount of a composition comprised of (i) mopidamol or an acid addition salt thereof and (ii) at least one pharmacologically acceptable acid or acid substance, the total amount of acid from acid addition salt present and acid or acid substance being in a ratio of at least about 1 acid equivalent to 1 mol of mopidamol.

These and other objects of the invention will become more apparent in the discussion below.

BRIEF DESCRIPTION OF THE INVENTION

Applicants have developed a novel mopidamol-containing pharmaceutical form which is characterized by exhibiting an improved bioavailability and substantially lower inter-individual and intra-individual fluctuations in blood level. These novel pharmaceutical preparations represent particular pharmokinetic advantages over previously known pharmaceutical forms.

More specifically, the pharmaceutical form of this invention is comprised of (i) mopidamol or an acid addition salt thereof and (ii) at least one pharmacologically acceptable acid or acid substance, the total amount of acid from acid addition salt present and acid or acid substance being in a ratio of at least about 1 acid equivalent to 1 mol of mopidamol. Other, conventional additives may optionally be present. This mopidamol preparation is characterized in that, irrespective of the physiological conditions in the gastrointestinal tract—for example, irrespective of the pH, the buffering effect, and the motility of this tract—it results in a high reproducible bioavailability of the mopidamole.

Figure 2:
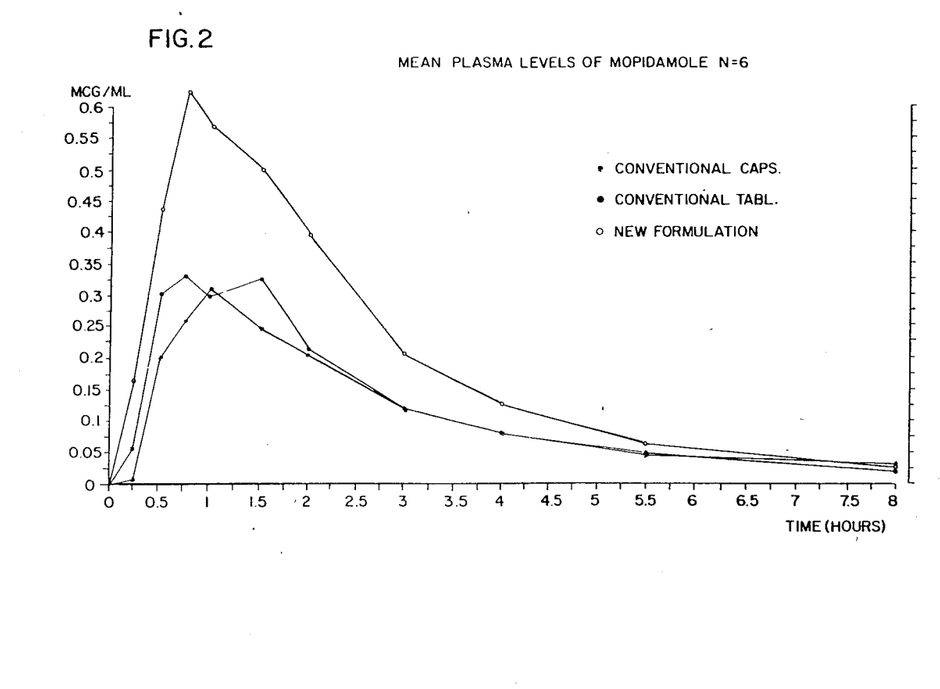
FIG. 2 represents a comparison of the release characteristics of two conventional mopidamol-containing pharmaceutical forms and of an embodiment of the invention. The release characteristics are shown by blood level curves.

The pharmaceutical forms according to the invention are distinguished in that they contain an intimate mixture of mopidamol or an acid addition salt thereof in the ratio of 1 mol of mopidamol or its acid addition salt to a total of at least about 1 acid equivalent of acid from acid addition salt present and from a pharmacologically acceptable acid or an acidly reacting substance (referred to collectively hereinafter as "acid present"). It was not to be expected that an excess of acid would suddenly lead to a significant increase in the bioavailability of the mopidamol. This increase is shown in FIG. 2, which sets forth blood-level values for a standard oral preparation, a film-coated tablet without any added acid, and a tablet containing 250 mg of added fumaric acid, according to the invention. There is a substantial increase in the speed of resorption and in the quantity of active substance resorbed.

Figure 1:
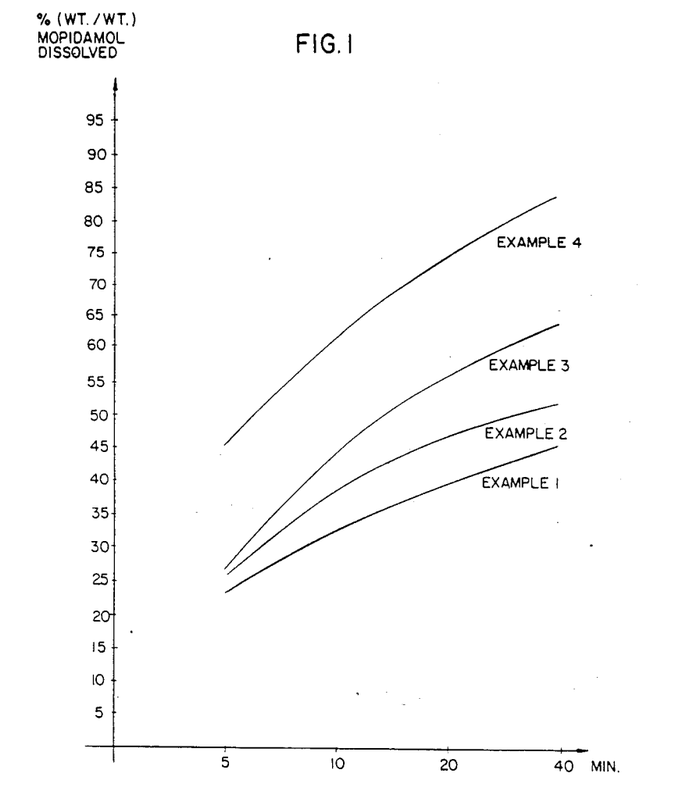
FIG. 1 represents the release characteristics at a pH of 6 of several different embodiments of the invention.

The dependency of the solubility or speed of dissolution of the mopidamol upon the quantity of acid added thereto has been investigated for different dosages. The two tables below and FIG. 1 show this dependence as it relates to mopidamol-containing film-coated tablets also containing differing amounts of primary sodium citrate or fumaric acid per tablet. The tablets were tested in vitro using the USP XX paddle method at 100 rpm in 500 ml of dilute McIlvain buffer with a pH of 6.

TABLE 1

Percentage release in vitro from film-coated tablets containing 250 mg of mopidamol each and varying amounts of fumaric acid in dilute buffer solution (pH 6)

| Amount of Fumaric | Percent of Mopidamol Released | |
|---|---|---|
| Acid (mg/tablet) | After 5 minutes | After 20 minutes |
| 0* | 25 | 40 |
| 50** | 43 | 77 |

TABLE 1-continued

Percentage release in vitro from film-coated tablets containing 250 mg of mopidamol each and varying amounts of fumaric acid in dilute buffer solution (pH 6)

| Amount of Fumaric Acid (mg/tablet) | Percent of Mopidamol Released | |
|---|---|---|
| | After 5 minutes | After 20 minutes |
| 125*** | 40 | 100 |

*See Example 1
**See Example 6
***See Example 7

TABLE 2

Percentage release in vitro from film-coated tablets containing 250 mg of mopidamol each and varying amounts of primary sodium citrate in dilute buffer solution (pH 6)

| Amount of Primary Sodium Citrate (mg/tablet) | Percent of Mopidamol Released | |
|---|---|---|
| | After 5 minutes | After 40 minutes |
| 0* | 25 | 40 |
| 25** | 30 | 58 |
| 50*** | 35 | 66 |
| 100**** | 48 | 84 |

*See Example 1
**See Example 2
***See Example 3
****See Example 4

It was not foreseeable that mopidamol which was present in only relatively small absolute quantities and was totally dissolved would form strongly supersaturated solutions and that this phenomenon would occur particularly if there is at least about 1 acid equivalent of acid present per mol of mopidamol. Another advantage of these preparations is that, due to the pH-independent solubility, the release profile and hence also the blood levels can be controlled without any loss in bioavailability.

The extremely surprising increase in relative bioavailability as compared with the standard oral preparation (mixture of mopidamol with fillers such as starch and lubricants such as magnesium stearate) may possibly arise from the fact that supersaturated and more highly concentrated solutions of active substance are formed.

Since mopidamol is a substance with a systemic activity, i.e., its therapeutic effect lasts only as long as maximum possible resorption is maintained, use of the mopidamol-containing pharmaceutical forms according to the invention results in a further improvement in the therapeutic activity. Thus, as a whole, use of the pharmaceutical forms according to the invention has the following advantages over use of conventional preparations:

1. Higher bioavailability.
2. Higher therapeutic reliability, which is achieved by the fact that, on the one hand, the inter-individual and intra-individual fluctuations which are typical of known forms are reduced and, on the other hand, totally inadequate blood level values are avoided.
3. By control of the release, it is possible to improve the therapeutic activity and to avoid side-effects at higher dosages.
4. In some cases the higher bioavailability makes it possible to reduce the dosage.

It has been found that the remarkable increase in the relative bioavailability of mopidamol can be achieved with a variety of pharmaceutical forms for oral administration. The essential prerequisite for the high blood levels is the determination of the correct ratio of acid present to mopidamol.

Extensive tests have shown that at least about 1 acid equivalent of acid present to 1 mol of mopidamol is required to obtain a significant improvement in the bioavailability of mopidamol. The quantity of acid present in relation to the mopidamol has no upper limit per se; it is limited only by the fact that if the quantity of acid present is too great, it is not possible to produce an oral form of mopidamol which can be easily swallowed. A ratio of from about 1 to 8 acid equivalents of acid present to 1 mol of mopidamol is preferred.

The acid addition salts of mopidamol comprise pharmacologically acceptable reaction products of mopidamol and inorganic or organic acids. Suitable such acids, which are well known to those skilled in the art, include hydrochloric acid, tartaric acid, and citric acid.

Useful acids or acid substances, that is, acidic excipients, comprise a plurality of toxicologically harmless, that is, pharmacologically acceptable, acids or acid substances. Suitable acids include, for example, fumaric acid, malic acid, tartaric acid, citric acid, succinic acid, ascorbic acid, adipic acid, and the like, and mixtures of any two or more of these acids. Suitable acid substances include monopotassium or monosodium salts of the aforementioned acids, such as, for example, monopotassium citrate or monopotassium tartarate, and acid salts selected from the group consisting of, for example, sodium or potassium bisulfate, betaine hydrochloride, and the like. Occasionally, anhydrides such as succinic anhydride, glutaric anhydride, or D-glucuronic acid-γ-lactone, which hydrolyze in the presence of water to form acids, may be used to increase the solubility of the mopidamol. Preparations containing fumaric acid, which are distinguished by their long shelf life, are preferred.

The ease with which optimum solid mopidamol preparations for oral administration can be produced was not foreseeable and was a complete surprise to anyone skilled in the art. According to the invention, preferred forms of mopidamol are produced, for example, by simply mixing mopidamol and fumaric acid together, with or without binders, and then compressing the mixture by means of tablet presses or roller compactors. The compressed masses are then broken up again by use of dry granulation equipment, and the resulting granules are transferred into hard gelatine capsules. The quantity of acidic excipients, the nature of these excipients, and the spectrum of particle sizes of the dry granulate are critical in achieving the optimum blood levels. In addition, mopidamol may be pelleted together with acidic excipients, and the pellets are sorted out and transferred into hard gelatine capsules.

The particle sizes of mopidamol-containing particles according to the invention are from about 0.1 to 2.0 mm, preferably from about 0.5 to 1.0 mm. This includes, for example, granules having particle sizes of from about 0.1 to 2.0 mm, preferably from about 0.25 to 1.25 mm, as well as pellets having particle sizes, that is, diameters, of from about 0.1 to 2.0 mm, preferably from about 0.5 to 1.5 mm.

Prior to insertion into hard gelatin capsules, mopidamol-containing granules or pellets can be coated with a lacquer coating which releases at least 90% of the active substance over a period of two hours in the gastrointestinal tract.

The active substance may also be combined with the acidic excipient and other additives which can be used directly in tablets and with the lubricant to form a mixture which can be made directly into tablets. This mixture is then compressed to form tablet cores which are subsequently covered with a coating to mask the flavor or a lacquer coating. If the lubricant is omitted and a film coating which delays release is used, the release of active substance can be spread over a longer period (cf. Example 15).

The active substance may also first be granulated with one or more acidic excipients, in a moist or dry state, and after the addition of further excipients, the granules are compressed to form tablet cores. However, it is also possible to first convert the active substance into a granulate with conventional excipients by wet or dry granulation and to subsequently add the acid excipients and a lubricant. Only then is the mass compressed to form tablet cores.

With respect to coatings, a flavor-masking coating may comprise any of the known pharmaceutically acceptable coatings such as, for example, hydroxypropyl methylcellulose. Suitable lacquer coatings include hydroxypropyl methylcellulose phthalate, copolymers of methacrylic acid and methacrylic acid ester, and mixtures thereof. The coatings may be present in amounts of from about 1 to 30% by weight, preferably from about 2 to 20% by weight, based upon the total weight of the coated granulate, pellets, or tablets.

Fumaric acid has proven to be a particularly suitable acid. It is physiologically non-toxic and easy to compress, and when combined with mopidamol, it does not produce a hydroscopic mixture. Its low solubility is essential to the invention; this ensures that, in the gastrointestinal tract, the mopidamol-containing particle is always surrounded by a sufficiently acidic microsphere in which the mopidamol, which does not dissolve readily, will dissolve safely and completely.

If, for medical reasons, it is desirable to have a maximum blood level which is less in intensity but at the same time longer in duration, there are a number of pharmaceutical possibilities. An increase in the amount of acid added leads to acceleration in the release of mopidamol, whereas a reduction slows down the release of active substance (cf. FIG. 1).

Other possible forms of mopidamol granulates differ in that, in addition to readily water-soluble binders such as polyvinylpyrrolidinone, excipients which form a mucilage in the presence of water, or even water-repellent excipients, may be added to the mopidamol and the acidic excipient. The solubility of the active substance and the stability of solutions thereof may be further improved by the addition of dissolution aids, such as fatty acid glycerol polyglycol esters (cf. Example 14).

If, on the other hand, a very rapidly rising blood level is required for the mopidamol, it is particularly advantageous to change the type of acid used, as well as to increase the quantity of acid added or to reduce the particle size of the granulate, thus enlarging the surface area. Due to the high solubility of each of tartaric acid, citric acid, malic acid, and ascorbic acid, in particular, the mopidamol dissolves completely in vitro in a short time, irrespective of the pH of the medium of release.

Formulations of mopidamol and acid may also be produced in tablet form surprisingly easily. It has been found that, even in the presence of conventional tablet-making excipients, the compressing operation during tablet making is sufficient to achieve a sufficiently intimate mechanical combination of active substance and added acid. The examples relating to tablets containing 25, 50, or 100 mg of primary sodium citrate to 250 mg of mopidamol and to tablets containing 50 or 125 mg of fumaric acid to 250 mg of mopidamol, illustrate this.

For flavoring purposes, the tablets were all covered with a thin coating of hydroxypropyl methylcellulose. It should be readily apparent to anyone skilled in the art that due to the nature and quantity of excipients added, the nature and quantity of acidic excipient, and the method of preparation (particle size of granulate), the release of the mopidamol active substance can be controlled within wide limits to suit the medical requirements.

In addition to the conventional excipients used, namely, polyvinylpyrrolidone, hydrogenated castor oil, and polyacrylic acid, it is also possible to use excipients such as methylcellulose, ethylcellulose, hydroxyethylcellulose, or hydroxypropyl methylcellulose. Furthermore, to achieve the desired release, mixtures consisting of mopidamol and acidic substances may be granulated with fats dissolved in organic solvents or with lacquers resistant to gastric juices such as cellulose acetate phthalate, shellac, and hydroxypropyl methylcellulose phthalate, and then compressed and broken up again into granules.

Figure 3:
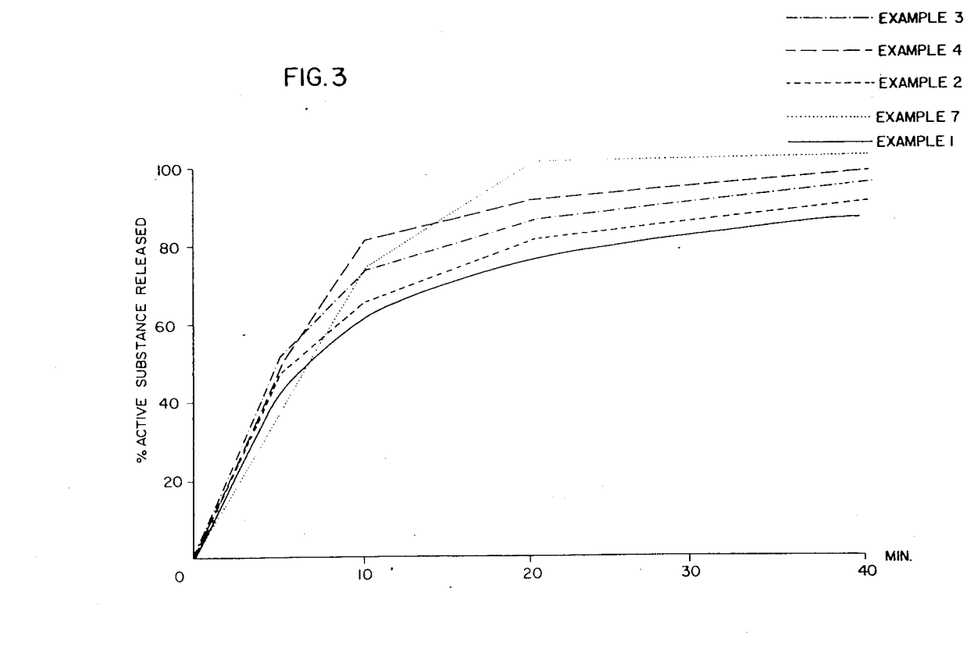
FIG. 3 represents the release characteristics at a pH of 4 of several different embodiments of the invention.

If, for therapeutic reasons, higher dosages of mopidamol are required and high blood level peaks should be avoided because of possible side effects, these requirements are met, according to the invention, by the formulations described in Example 15. Since these formulations release the active substance in controlled manner, for example, over a period of from about 1 to 2 hours, the small particles are already located to a great extent in the duodenum, that is, in a pH range of above pH 4.0 (cf. also FIG. 3, which shows the rate of dissolution at a pH of 4).

Therefore, these forms must release the active substance in a pH medium in which the active substance is virtually no longer soluble, in the biological sense. If the release of mopidamol is delayed any longer, that is, if the small units of mopidamol pass into lower sections of the intestines, there is no longer any guarantee of total dissolution and absorption. The optimum absorption of mopidamol is achieved, according to the invention, by accurately adapting the correlations between the nature and quantity of acidic excipient, the nature of the additives, and the method of processing to the rate of release of active substance required.

IN VIVO TESTING IN MAN OF THE FORMS ACCORDING TO THE INVENTION

All the tests were made on healthy volunteers, mostly in the form of cross-over tests. Since mopidamol is only excreted in the urine to a very small extent, the only biological parameter used was the blood level, which was determined by fluorescence measurement.

Various pharmaceutical forms were tested on humans. However, since the oral pharmaceutical forms according to the invention without delayed release do not differ significantly from one another in vivo, FIG. 2 and Tables 3 and 4 only show the results pertaining to the formulation of Example 11.

FIG. 2 shows the average mopidamol blood levels of six test subjects after administration of a preparation according to the invention and two conventional preparations, respectively. It can be seen that substantially higher blood level values were obtained with the acid-containing pharmaceutical formulation according to the invention than with the conventional formulations.

A comparison of the values of the area under the blood level curve (AUC) of conventional tablets or capsules with the formulation according to the invention and the relative bioavailabilities, are shown in the following table:

TABLE 3

COMPARISON OF AUC VALUES AND RELATIVE BIOAVAILABILITY

| Test Subject No. | AUC | | | Rel. Bioavail. (%) | |
| --- | --- | --- | --- | --- | --- |
| | Tablet | Capsule | New Form | Tab./new | Caps./new |
| 1 | 0.027 | 0.073 | 0.675 | 2500 | 924 |
| 2 | 2.173 | 1.754 | 1.89 | 87 | 108 |
| 3 | 1.742 | 2.002 | 1.431 | 82 | 71 |
| 4 | 0.232 | 0.177 | 1.631 | 703 | 921 |
| 5 | 2.496 | 1.656 | 3.768 | 151 | 228 |
| 6 | 0.690 | 1.881 | 1.465 | 212 | 78 |

The blood levels of the individual test subjects and Table 3 show that there is a very sharp increase in the blood level, particularly at low values of the standard commercial preparations, that is, of the conventional tablets or capsules and in the "non-absorbers" (who occur from time to time), whereas in test subjects who show good blood levels even with the standard commercial preparations there is only a relatively slight change. This significantly reduces the fluctuations in blood levels which are otherwise normally found and which make therapy more difficult.

The reduction in blood level fluctuation is also demonstrated by a comparison of the coefficients of variation of standard commercial forms and the formulation according to the invention (new form) set forth in the table below. The coefficients of variation of the new form have significantly lower values.

TABLE 4

Comparison of the variation coefficients of standard commercial forms and a pharmaceutical form according to the invention

| Test Subject No. | Time (hrs.) | Variation coefficient | | |
| --- | --- | --- | --- | --- |
| | | Tablet | Capsule | New Form |
| 1 | 0.25 | 244.7 | 69.7 | 75.8 |
| 2 | 0.50 | 155.7 | 111.9 | 47.2 |
| 3 | 0.75 | 130.8 | 97.1 | 63.0 |
| 4 | 1.00 | 96.1 | 89.0 | 55.1 |
| 5 | 1.50 | 90.3 | 96.5 | 43.4 |
| 6 | 2.00 | 97.4 | 92.9 | 44.0 |
| 7 | 3.00 | 95.6 | 84.5 | 52.0 |
| 8 | 4.00 | 83.9 | 75.7 | 60.0 |
| 9 | 5.50 | 110.8 | 67.5 | 66.5 |
| Area (mcg × Time/ml) | — | 85.4 | 70.4 | 57.5 |

The following examples are intended to illustrate the invention and should not be construed as limiting the invention thereto.

EXAMPLES

Example 1

Each tablet had the following composition:

| Component | Weight (mg) |
| --- | --- |
| (1) Mopidamol | 250.0 |
| (2) Powdered lactose | 91.0 |
| (3) Corn starch | 37.0 |
| (4) Cross-linked polyvinylpyrrolidone | 10.0 |
| (5) AEROSIL ® | 3.0 |
| (6) Powdered triglyceride | 6.0 |
| (7) Magnesium stearate | 3.0 |
| Total: | 400.0 |

Preparation of 1000 tablets

Components (1) to (5) were admixed, the mixture was moistened with 125 mg of demineralized water, and the moistened misture was passed through a screen with a mesh size of 1.6 mm. The granulate was dried in a circulating air dryer at a temperature of 45° C., and then it was passed through the same screen again. Next, components (6) and (7), which had been finely screened, were added and mixed in, and the mixture was compressed.

Diameter of punch: 11 mm
Radius of curvature: 11 mm

The tablets were provided with a flavor-masking coating of hydroxypropyl methylcellulose. The finished film-coated tablets each weighed about 4 mg more than the uncoated tablets.

Example 2

Each tablet had the following composition:

| Component | Weight (mg) |
| --- | --- |
| (1) Mopidamol | 250.0 |
| (2) Lactose | 91.0 |
| (3) Corn starch | 37.0 |
| (4) Cross-linked polyvinylpyrrolidone | 10.0 |
| (5) AEROSIL | 3.0 |
| (6) Sodium dihydrogen citrate | 25.0 |
| (7) Powdered triglyceride | 6.0 |
| (8) Magnesium stearate | 3.0 |
| Total: | 425.0 |

Preparation

Components (1) to (5) were mixed as in Example 1. The mixture was moistened, dried, and screened, and Components (6) to (8), finely screened, were added. The mixture was compressed.

Diameter of punch: 11 mm
Radius of curvature: 11 mm

The tablets were provided with a flavor-masking coating of hydroxypropyl methylcellulose. The finished film-coated tablets each weighed about 4.25 mg more than the uncoated tablets.

Example 3

Each tablet had the following composition:

| Component | Weight (mg) |
| --- | --- |
| (1) Mopidamol | 250.0 |
| (2) Lactose | 91.0 |
| (3) Corn starch | 37.0 |
| (4) Cross-linked polyvinylpyrrolidone | 10.0 |
| (5) AEROSIL | 3.0 |
| (6) Sodium dihydrogen citrate | 50.0 |
| (7) Powdered triglyceride | 6.0 |
| (8) Magnesium stearate | 3.0 |
| Total: | 450.0 |

Preparation

Components (1) to (5) were mixed together as described in Example 1. The mixture was moistened, dried, and screened, and components (6) to (8) were finely screened and added. The mixture was compressed.

Diameter of punch: 11 mm
Radius of curvature: 11 mm

The tablets were provided with a flavor-masking coating of hydroxypropyl methylcellulose. The finished film-coated tablets each weighed about 4.5 mg more than the uncoated tablets.

Example 4

Each tablet had the following composition:

| Component | Weight (mg) |
| --- | --- |
| (1) Mopidamol | 250.0 |
| (2) Lactose | 91.0 |
| (3) Corn starch | 37.0 |
| (4) Cross-linked polyvinylpyrrolidone | 10.0 |
| (5) AEROSIL | 3.0 |
| (6) Sodium dihydrogen citrate | 100.0 |
| (7) Powdered triglyceride | 6.0 |
| (8) Magnesium stearate | 3.0 |
| Total: | 500.0 |

Preparation

Components (1) to (5) were mixed together as described in Example 1. The mixture was moistened, dried, and screened, and components (6) to (8) were finely screened and added. The mixture was compressed.

Diameter of punch: 11 mm
Radius of curvature: 11 mm

The tablets were provided with a flavor-masking coating of hydroxypropyl methylcellulose. The finished film-coated tablets each weighed about 5.0 mg more than the uncoated tablets.

Example 5

Each capsule had the following contents:

| Component | Weight (mg) |
| --- | --- |
| (1) Mopidamol | 250.0 |
| (2) Fumaric acid | 250.0 |
| (3) Corn starch | 37.0 |
| (4) Cross-linked polyvinylpyrrolidone | 10.0 |
| (5) Lactose | 91.0 |
| (6) AEROSIL | 3.0 |
| (7) Powdered triglyceride | 6.0 |
| (8) Magnesium stearate | 3.0 |
| Total: | 650.0 |

Preparation of 1000 capsules

Components (1) and (2) were mixed together and moistened with 50 gm of ethanol, and the moistened mixture was passed through a screen with a mesh size of 1.6 mm and dried. After drying, this material was passed again through the same screen, and components (3) to (8) were finely screened and added thereto. The resulting mixture was packed into size 000 gelatine capsules.

Example 6

Each tablet had the following composition:

| Component | Weight (mg) |
| --- | --- |
| (1) Mopidamol | 250.0 |
| (2) Lactose | 91.0 |
| (3) Corn starch | 37.0 |
| (4) Cross-linked polyvinylpyrrolidone | 10.0 |
| (5) AEROSIL | 3.0 |
| (6) Fumaric acid | 50.0 |
| (7) Powdered triglyceride | 6.0 |
| (8) Magnesium stearate | 3.0 |
| Total: | 450.0 |

Preparation

Components (1) to (5) were mixed together as described in Example 1. The mixture was moistened, dried, and screened, and components (6) to (8) were finely screened and added. The mixture was compressed.

Diameter of punch: 11 mm
Radius of curvature: 11 mm

The tablets were provided with a flavor-masking coating of hydroxypropyl methylcellulose. The finished film-coated tablets each weighed about 4.5 mg more than the uncoated tablets.

Example 7

Each tablet had the following composition:

| Component | Weight (mg) |
| --- | --- |
| (1) Mopidamol | 250.0 |
| (2) Lactose | 91.0 |
| (3) Corn starch | 37.0 |
| (4) Cross-linked polyvinylpyrrolidone | 10.0 |
| (5) AEROSIL | 3.0 |
| (6) Fumaric Acid | 125.0 |
| (7) Powdered triglyceride | 6.0 |
| (8) Magnesium stearate | 3.0 |
| Total: | 525.0 |

Preparation

Components (1) to (5) were mixed together as described in Example 1. The mixture was moistened, dried, and screened, and components (6) to (8) were finely screened and added. The mixture was compressed.

Diameter of punch: 11 mm
Radius of curvature: 11 mm

The tablets were provided with a flavor-masking coating of hydroxypropyl methylcellulose. The finished film-coated tablets each weighed about 5.25 mg more than the uncoated tablets.

Example 8

Each tablet had the following composition:

| Component | Weight (mg) |
| --- | --- |
| (1) Mopidamol | 250.0 |
| (2) Lactose | 91.0 |
| (3) Corn starch | 37.0 |
| (4) Cross-linked polyvinylpyrrolidone | 10.0 |
| (5) AEROSIL | 3.0 |
| (6) Tartaric acid | 20.0 |
| (7) Powdered triglyceride | 6.0 |
| (8) Magnesium stearate | 3.0 |
| Total: | 420.0 |

Preparation

Components (1) to (5) were mixed together as described in Example 1. The mixture was moistened, dried, and screened, and components (6) to (8) were finely screened and added. The mixture was compressed.

Diameter of punch: 11 mm
Radius of curvature: 11 mm

The tablets were provided with a flavor-masking coating of hydroxypropyl methylcellulose. The finished film-coated tablets each weighed about 4.2 mg more than the uncoated tablets.

Example 9

Each tablet had the following composition:

| Component | Weight (mg) |
| --- | --- |
| (1) Mopidamol | 250.0 |
| (2) Lactose | 91.0 |
| (3) Corn starch | 37.0 |
| (4) Cross-linked polyvinylpyrrolidone | 10.0 |
| (5) AEROSIL | 3.0 |
| (6) Tartaric acid | 45.0 |
| (7) Powdered triglyceride | 6.0 |
| (8) Magnesium stearate | 3.0 |
| Total: | 445.0 |

Preparation

Components (1) to (5) were mixed together as described in Example 1. The mixture was moistened, dried, and screened, and components (6) to (8) were finely screened and added. The mixture was compressed.

Diameter of punch: 11 mm
Radius of curvature: 11 mm

The tablets were provided with a flavor-masking coating of hydroxypropyl methylcellulose. The finished film-coated tablets each weighed about 4.5 mg more than the uncoated tablets.

Example 10

Each tablet had the following composition:

| Component | Weight (mg) |
| --- | --- |
| (1) Mopidamol | 250.0 |
| (2) Lactose | 91.0 |
| (3) Corn starch | 37.0 |
| (4) Cross-linked polyvinylpyrrolidone | 10.0 |
| (5) AEROSIL | 3.0 |
| (6) Tartaric acid | 90.0 |
| (7) Powdered triglyceride | 6.0 |
| (8) Magnesium stearate | 3.0 |
| Total: | 490.0 |

Preparation

Components (1) to (5) were mixed together as described in Example 1. The mixture was moistened, dried, and screened, and components (6) to (8) were finely screened and added. The mixture was compressed.

Diameter of punch: 11 mm
Radius of curvature: 11 mm

The tablets were provided with a flavor-masking coating of hydroxypropyl methylcellulose. The finished film-coated tablets each weighed about 4.9 mg more than the uncoated tablets.

Example 11

Each tablet had the following composition:

| Component | Weight (mg) |
| --- | --- |
| (1) Mopidamol | 250.0 |
| (2) Lactose | 91.0 |
| (3) Corn starch | 37.0 |
| (4) Cross-linked polyvinylpyrrolidone | 10.0 |
| (5) AEROSIL | 3.0 |
| (6) Fumaric acid | 250.0 |
| (7) Powdered triglyceride | 6.0 |
| (8) Magnesium stearate | 3.0 |
| Total: | 650.0 |

Preparation

Components (1) to (5) were mixed together as described in Example 1. The mixture was moistened, dried, and screened, and components (6) to (8) were finely screened and added. The mixture was compressed.

Diameter of punch: 11 mm
Radius of curvature: 11 mm

The tablets were provided with a flavor-masking coating of hydroxypropyl methylcellulose. The finished film-coated tablets each weighed about 6.5 mg more than the uncoated tablets.

Example 12

Each tablet had the following composition:

| Component | Weight (mg) |
| --- | --- |
| (1) Mopidamol | 250.0 |
| (2) Fumaric acid | 250.0 |
| (3) Carboxymethylcellulose | 97.0 |
| (4) Polyvinyl acetate | 20.0 |
| (5) Magnesium stearate | 3.0 |
| Total: | 620.0 |

Preparation of 1000 film-coated tablets

Components (1) to (3) were mixed together and moistened with a solution of component (4) in 100 ml of acetone. The damp mixture was passed through a screen with a mesh size of 1.6 mm, dried, and passed through the same screen again. Then, component (5) was added. The finished granulate was compressed to form tablets.

Punch: 12 mm
Radius of curvature: 10 mm

The tablets were provided with a flavor-masking coating of hydroxypropyl methylcellulose. This increased the weight of the film-coated tablets by about 6.2 mg apiece.

Example 13

Each tablet had the following composition:

| Component | Weight (mg) |
| --- | --- |
| (1) Mopidamol | 250.0 |
| (2) Tartaric acid | 45.0 |
| (3) Lactose | 91.0 |
| (4) Corn starch | 37.0 |
| (5) Cross-linked polyvinylpyrrolidone | 10.0 |

| Component | Weight (mg) |
|---|---|
| (6) AEROSIL | 3.0 |
| (7) Powdered triglyceride | 6.0 |
| (8) Magnesium stearate | 3.0 |
| Total: | 445.0 |

Preparation of 1000 film-coated tablets

Components (1) and (2) were triturated and moistened with 50 ml of acetone and then further processed as described in Example 1. Ingredients (3) to (8) were finely screened and added thereto. The mixture was compressed.

Diameter of punch: 11 mm
Radius of curvature: 11 mm

The tablets were provided with a flavor-masking coating of hydroxypropyl methylcellulose. The finished film-coated tablets each weighed about 4.5 mg more than the uncoated tablets.

Example 14

Each capsule contained the following:

| Component | Weight (mg) |
|---|---|
| (1) Mopidamol | 250.0 |
| (2) Fumaric acid | 250.0 |
| (3) CREMOPHOR RH 40 ® | 200.0 |
| (4) Microcrystalline cellulose | 150.0 |
| (5) Pyrogenic silicic acid | 50.0 |
| Total: | 900.0 |

Preparation of 1000 capsules

Components (1) and (2) were thoroughly triturated in component (3), and then component (4) and finally component (5) were added. The finished trituration was packed into size 000 capsules.

Example 15

Oblong tablets with delayed release of the active substance were prepared. The tablets had the following composition:

| Component | Weight (kg) |
|---|---|
| (1) Mopidamol | 3.00 |
| (2) Fumaric acid | 2.50 |
| (3) Pyrogenic silicic acid | 0.20 |
| Total: | 5.70 |

The above ingredients were mixed together, compressed in a roller compactor, and granulated. After 0.06 kg of magnesium stearate had been added, the mixture was compressed into oblong tablets. These were sprayed with a solution of methacrylic acid/methacrylic acid ester copolymer and hydroxypropylmethyl cellulose phthalate in a ratio of 2:8 (acetone/iospropanol 1:1) until an intact diffusion membrane formed.

Example 16

The granulate prepared according to Example 15, by use of a roller compactor and subsequent dry granulation, was mixed with 0.5% magnesium stearate and packed into hard gelatine capsules.

Example 17

Hard gelatine capsules were filled with pellets having the following composition:

| Component | Weight (mg) |
|---|---|
| (1) Tartaric acid | 165.0 |
| (2) Mopidamol | 200.0 |
| (3) Fumaric acid | 105.0 |
| (4) Polyvinyl pyrrolidone | 44.0 |
| (5) Talc | 16.0 |
| (6) Hydroxypropyl methyl-cellulose | 7.0 |
| Total: | 537.0 |

Preparation

Spherical tartaric acid crystals (1) were coated with component (6). After being moistened with component (4), dissolved in isopropanol, the crystals were coated in small batches with a powdered mixture of components (2), (3), and (5) in a suitable coating vessel. After all the powder mixture had been applied, the resulting pellets are screened, dried, and packed into hard gelatine capsules.

Example 18

Hard gelatine capsules were filled with pellets having the following composition:

| Component | Weight (mg) |
|---|---|
| (1) Citric acid | 150.0 |
| (2) Mopidamol | 200.0 |
| (3) Fumaric acid | 105.0 |
| (4) Polyvinylpyrrolidone | 30.0 |
| (5) Talc | 16.0 |
| (6) Polyoxyethylene-hydrogenated castor oil | 29.0 |
| (7) Hydroxypropyl methyl-cellulose | 7.0 |
| Total: | 537.0 |

In accordance with the procedure described in Example 17, the isolated citric acid crystals were coated with a mixture of components (2), (3), (5) and (6) using dissolved component (4). The screened pellets were packed into hard gelatine capsules.

Example 19

Pellets prepared according to Example 18 were sprayed with a solution of hydroxypropyl methyl-cellulose phthalate (acetone/isopropanol (3:7)), dried, and then packed into hard gelatine capsules.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A composition which comprises a pharmaceutical capsule vehicle filled with granules or pellets of (i) mopidamol or an acid addition salt thereof and (ii) at least one pharmacologically acceptable acid or acid substance, the total amount of acid from acid addition salt present and acid or acid substance being in a ratio of at least 1 acid equivalent to 1 mol of mopidamol.

2. The composition of claim 1, wherein the total amount of acid from acid addition salt present and acid or acid substance is in a ratio of from about 1 to 8 acid equivalents to 1 mol of mopidamol.

3. The composition of claim 1, wherein the pharmacologically acceptable acid or acid substance is selected from the group consisting of tartaric acid, citric acid, fumaric acid, succinic acid, malic acid, ascorbic acid, adipic acid, sodium or potassium salts of said acids, sodium or potassium hydrogen sulfate, betaine hydrochloride, anhydrides of succinic or glutaric acid which hydrolyse in water to form acids, D-glucuronic acid-γ-lactone, and mixtures thereof.

4. The method of claim 1, wherein the pharmacologically acceptable acid or acid substance is fumaric acid.

5. The composition of claim 1, wherein the pharmaceutical vehicle is filled with granules having a particle size of from about 0.1 to 2.0 mm.

6. The composition of claim 5, wherein the granules have a particle size of from about 0.25 to 1.25 mm.

7. The composition of claim 5, wherein the granules are contained in hard gelatine capsules.

8. The composition of claim 7, wherein the granules have a delayed-release coating which permits the release of at least 90% of the mopidamol in the gastrointestinal tract over a period of two hours.

9. The composition of claim 1, wherein the pharmaceutical vehicle is filled with pellets having a diameter of from about 0.1 to 2.0 mm.

10. The composition of claim 9, wherein the pellets have diameters of from about 0.5 to 1.5 mm.

11. The composition of claim 9, wherein the pellets are contained in hard gelatine capsules.

12. The composition of claim 11, wherein the pellets have a delayed-release coating which premits the release of at 90% of the mopidamol in the gastrointestinal tract over a period of two hours.

13. The composition of claim 1, wherein the granules or pellets also comprise conventional pharmacological additives.

14. The composition of claim 13, wherein the additives are selected from the group consisting of water-soluble binders, mucilaginous excipients, water-dissolution aids, and mixtures thereof.

15. The composition of claim 14, wherein the additives are selected from the group consisting of methylcellulose, ethylcellulose, hydroxyethylcellulose, hydroxypropyl methylcellulose, polyacrylic acids, fats, and mixtures thereof.

16. The composition of claim 1, wherein the composition is in the form of particles having a coating comprised of a lacquer which permits the release of at least 90% of the mopidamol in the gastrointestinal tract over a period of two hours.

17. The compositon of claim 1, wherein the granules or pellets contain fatty acid glycerol polyglycol esters as dissolution aids.

18. The composition of claim 1, wherein some of the acid or acid substance is coated with a coating of hydroxyethylcellulose or hydroxypropyl methylcellulose, which coating permits the release of at least 90% of the mopidamol in the gastrointestinal tract over a period of two hours, and then the mopidamol and other additives are applied thereto.

19. The composition of claim 18, wherein the resulting pellets are provided with a coating and/or are packed into hard gelatine capsules.

20. A method for the treatment of cardiovascular disorders or thrombosis in a host in need of such treatment which comprises administering to said host a cardiovascularly or antithromboticly effective amount of a composition of claim 1.

* * * * *